United States Patent [19]

Barnes et al.

[11] 4,078,078

[45] Mar. 7, 1978

[54] NOVEL XANTHONE-2-CARBOXYLIC ACID COMPOUNDS

[75] Inventors: Alan Charles Barnes; Peter Wilfred Hairsine; Peter John Ramm, all of Swindon; John Bodenham Taylor, Down Ampney, near Cirencester, all of England

[73] Assignee: Roussel UCLAF, Paris, France

[21] Appl. No.: 770,302

[22] Filed: Feb. 22, 1977

Related U.S. Application Data

[62] Division of Ser. No. 592,176, Jul. 1, 1975, Pat. No. 4,024,276.

[30] Foreign Application Priority Data

| | | |
|---|---|---|
| Jul. 9, 1974 | United Kingdom | 30428/74 |
| May 16, 1975 | United Kingdom | 20876/75 |

[51] Int. Cl.[2] .............. C07D 311/86

[52] U.S. Cl. .............. 424/283; 260/308 D; 260/335

[58] Field of Search .............. 260/335; 424/283

[56] References Cited

U.S. PATENT DOCUMENTS 3,849,565 11/1974 Pfister et al. .............. 424/283

*Primary Examiner*—Norma S. Milestone
*Attorney, Agent, or Firm*—Hammond & Littell

[57] ABSTRACT

Novel xanthone-2-carboxylic acid compounds of the formula

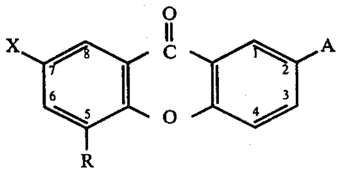

I wherein A is selected from the group consisting of —COOR', a 1H-tetrazol-5-yl and a 1H-tetrazolylcarbamoyl, R' is selected from the group consisting of hydrogen, alkyl of 1 to 5 carbon atoms and cation of a non-toxic, pharmaceutically acceptable organic or inorganic base, R is selected from the group consisting of hydrogen, alkyl of 1 to 9 carbon atoms, alkoxy of 1 to 9 carbon atoms and alkoxy alkoxy of 2 to 9 carbon atoms and X is selected from the group consisting of

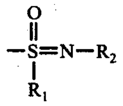

Ia and

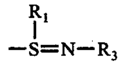

Ib wherein $R_1$ is alkyl of 1 to 5 carbon atoms, $R_2$ is selected from the group consisting of hydrogen, acyl of an aliphatic acid of 1 to 5 carbon atoms, aroyl of 7 to 8 carbon atoms, araliphatic acyl with 1 to 5 carbon atoms in the aliphatic portion and 6 or 7 carbon atoms in the aryl portion, aralkyl of 7 to 8 carbon atoms, arylsulfonyl, a carbamoyl, a carboxyalkyl of 1 to 5 carbon atoms, —CO—$(CH_2)_n$— Het where *n* is 1,2 or 3 and Het is a N-attached nitrogen heterocyclic which may contain an additional heteroatom and

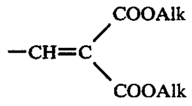

and Alk is alkyl of 1 to 5 carbon atoms and $R_3$ is arylsulfonyl which possess anti-allergic properties and their preparation.

6 Claims, No Drawings

NOVEL XANTHONE-2-CARBOXYLIC ACID COMPOUNDS

PRIOR APPLICATION

This application is a division of our copending, commonly assigned U.S. Patent application Ser. No. 592,176 filed July 1, 1975, now U.S. Pat. No. 4,024,276.

OBJECTS OF THE INVENTION

It is an object of the invention to provide the novel xanthone-2-carboxylic acid compounds of formula I and to provide a novel method of preparing the said compounds.

It is another object of the invention to provide novel compositions for treating allergic conditions.

It is another object of the invention to provide a novel method of relieving allergic conditions in warm-blooded animals.

These and other objects and advantages of the invention will become obvious from the following detailed description. THE INVENTION The novel xanthone-2-carboxylic acid compounds of the invention have the formula

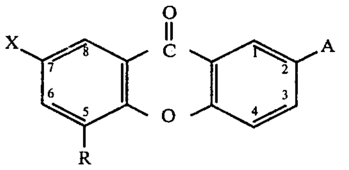

I wherein A is selected from the group consisting of —COOR', a 1H-tetrazol-5-yl and a 1H-tetrazolylcarbamoyl, R' is selected from the group consisting of hydrogen, alkyl of 1 to 5 carbon atoms and cation of a non-toxic, pharmaceutically acceptable organic or inorganic base, R is selected from the group consisting of hydrogen, alkyl of 1 to 9 carbon atoms, alkoxy of 1 to 9 carbon atoms and alkoxy alkoxy of 2 to 9 carbon atoms and X is selected from the group consisting of

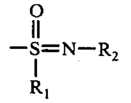

Ia and

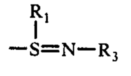

Ib wherein $R_1$ is alkyl of 1 to 5 carbon atoms, $R_2$ is selected from the group consisting of hydrogen, acyl of an aliphatic acid of 1 to 5 carbon atoms, aroyl of 7 to 8 carbon atoms, araliphatic acyl with 1 to 5 carbon atoms in the aliphatic portion and 6 or 7 carbon atoms in the aryl portion, aralkyl of 7 to 8 carbon atoms, arylsulfonyl, a carbamoyl, a carboxyalkyl of 1 to 5 carbon atoms,—$CO—(CH_2)_n—$Het where $n$ is 1,2 or 3 and Het is a N-attached nitrogen heterocyclic which may contain an additional heteroatom and

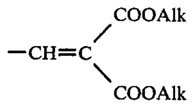

and Alk is alkyl of 1 to 5 carbon atoms and $R_3$ is arylsulfonyl.

Among the preferred substituents of formula I, A is preferably —COOR' especially when $R_1$ is methyl and $R_2$ is hydrogen, acetyl, benzoyl or p-toluenesulfonyl or $R_3$ is p-toluenesulfonyl and R is preferably hydrogen or an alkyl or alkoxy of 4 to 7 carbon atoms such as n-hexyl or n-pentyloxy. X is preferably a group wherein $R_1$ is methyl, $R_3$ is p-toluenesulfonyl, R is hydrogen or alkyl or alkoxy of 4 to 7 carbon atoms and $R_2$ is hydrogen, benzoyl, acetyl, benzyl, p-toluenesulfonyl, morpholinoacetyl, piperidinoacetyl, carbamoyl, carboxymethyl, carboxyethyl or 2', 2'-bisethoxycarbonylethenyl.

Particularly preferred compounds of the invention are 7-(S-methylsulfonimidoyl)-xanthone-2-carboxylic acid; 7-(N-acetyl-S-methylsulfonimidoyl)-xanthone-2-carboxylic acid; 7-(N-benzoyl-S-methylsulfonimidoyl)-xanthone-2-carboxylic acid; 7-/N-(N'-morpholinoacetyl)-S-methylsulfonimidoyl/-xanthone-2-carboxylic acid; 7-(N-p-toluenesulfonyl-S-methylsulfonimidoyl) -xanthone-2-carboxylic acid; 7-(N-Carbamoyl-S-methylsulfonimidoyl)-xanthone-2-carboxylic acid 7-(N-[2',2'-bisethoxycarbonylethenyl]-S-methylsulfonimidoyl)-xanthone-2-carboxylic acid; 7-(N-p-toluenesulfonyl-S-methylsulfimidoyl)-xanthone-2-carboxylic acid; 7-(S-methylsulfonimidoyl)-5-(n-hexyl)-xanthone-2-carboxylic acid; 7-(S-methylsulfonimidoyl)-5-(n-pentyloxy)-xanthone-2-carboxylic acid, and 7-(N-carbamoyl-S-methylsulfonimidoyl)-5-(n-hexyl)-xanthone-2-carboxylic acid, and their salts with non-toxic, pharmaceutically acceptable organic and inorganic bases and their lower alkyl esters.

As indicated above, salts of the compounds of the invention may be formed with organic or inorganic bases. Suitable inorganic bases include alkali metal and alkali earth metal hydroxides such as sodium, potassium, lithium or calcium hydroxides, magnesium hydroxide or ammonium hydroxide. Suitable organic bases include substituted or unsubstituted alkylamines such as trimethylamine, methylamine, propylamine, N,N-dimethylethanolamine or tris(hydroxymethyl)-methylamine; basic amino acids such as lysine or arginine; or other bases such as glucosamine or procaine.

The compounds of the invention may be prepared by any convenient method. According to a further feature of the invention, we provide a process for the preparation of esters of compounds of formula I in which A represents a carboxy group, R is as defined and X is a group of formula Ia in which $R_1$ is as defined, and $R_2$ is hydrogen, comprising reacting a compound of the formula

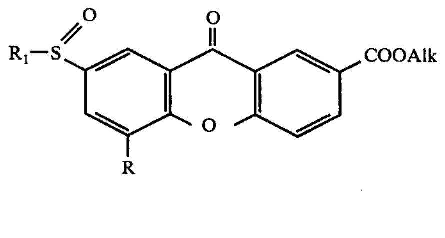

III where R and $R_1$ are as defined and Alk is an alkyl group with 1 to 5 carbon atoms with an alkali metal azide or with a hydrocarbon-sulfonyloxylamine, to form a compound of the formula

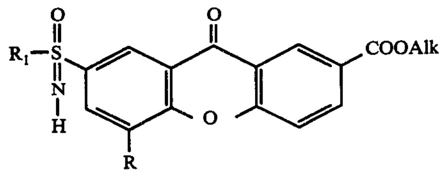

IV where R, $R_1$ and Alk are as defined above for formula III.

The reaction with the azide is preferably effected in an anhydrous acid medium, advantageously in polyphosphoric acid, at an elevated temperature such as 40° to 100° C, especially about 60° C. The azide is advantageously sodium azide. The hydrocarbon sulfonyloxylamine is preferably an aromatic sulfonyloxy compound such as mesitylene sulfonyloxylamine and the reaction is conveniently effected at room temperature such as in the range of 10° to 30° C in the presence of an inert solvent, such as a chlorinated hydrocarbon solvent such as dichloromethane.

Compounds of formula I in which X has the formula Ia and $R_2$ is other than hydrogen can be prepared by reaction of the compound of formula IV with reagents to introduce the required $R_2$ group. This may be accomplished, for example, by the following methods.

a. Reaction of the compound of formula IV with an active halide or, where acyl, with an acid anhydride of the radical $R_2$, where $R_2$ is an aliphatic acyl, aroyl, aralkyl, carboxyalkyl, or arylsulfonyl group, the halide preferably being the chloride, whereby the corresponding compound of formula I is obtained. The reaction is advantageously effected in an inert solvent, preferably in the presence of a base such as a tertiary amine. Alternatively, the base such as pyridine may constitute the reaction medium. The reaction is preferably effected at an elevated temperature such as on a steam bath.

b. Reaction of the compound of formula IV with a reactive derivative of the radical $—CO—(CH_2)_n—Hal$ where Hal is chlorine, bromine or iodine followed by reaction with a nitrogen heterocyclic H.Het yields a compound of formula I in which $R_2$ represents a group $—CO—(CH_2)_nHet$ where *n* and Het are as defined above. The reactive derivative is conveniently the halide, such as the chloride or bromide or the anhydride. This reaction is conveniently effected under similar conditions to those used for reaction (a); reaction with the heterocyclic compound is conveniently effected in an inert solvent such as halogenated hydrocarbon.

c. Reaction of the compound of formula IV with an alkali metal cyanate followed by hydration yields a compound of formula I in which $R_2$ is a carbamoyl. The reaction with the cyanate, preferably sodium cyanate, is conveniently effected in an acid medium such as acetic acid at ambient temperature followed by work-up in an aqueous medium.

d. Reaction of the compound of formula IV with a dialkyl alkoxymethylenemalonate of the formula AlkO-$CH{=}C(CO\text{-}OAlk)_2$, where Alk is alkyl of 1 to 5 carbon atoms yields a compound of formula I in which $R_2$ is a $—CH{=}C(COOAlk)_2$. The reaction is preferably effected in the absence of a solvent using an excess of the malonate at an elevated temperature such as 100°—150° C. Esters of compounds of formula I in which A is a carboxy group, R is as defined and X has formula Ib may be prepared by reaction of a compound of the formula

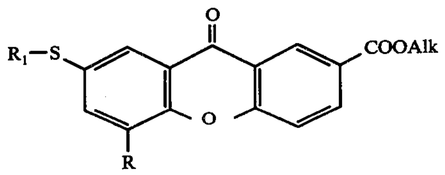

II where $R_1$, $R_-$ and $Alk_+$ are as defined, with a reagent of the formula $R_3$—N—Cl Na, where $R_3$ is as defined such as a sodium N-chloroarylsulfonamide. The reaction is conveniently effected in an inert aqueous medium such as a dioxane-water mixture at a moderately elevated temperature, such as at the reflux temperature of the medium.

Any of the above-mentioned products can then be converted into the free 2-carboxylic acids by simple hydrolysis, especially basic hydrolysis such as by using aqueous alcohol sodium hydroxide. Other esters can be prepared by esterifying the free acid. However, as the free acids are rather insoluble in most solvents, it is advantageous to use a polar aprotic solvent such as dimethylformamide and the halide of the esterifying alcohol in the presence of a base. Thus, for example, treatment of the free acid in dimethylformamide with an alkyl chloride or bromide in the presence of an alkali metal carbonate, such as lithium carbonate, yields the desired alkyl ester. Salts of the free acids may be prepared by simple reaction of the acid with an organic or inorganic base.

Compounds of formula I in which A is a 1H-tetrazoly group may be prepared from the corresponding carboxylic acid by the following route. The free acid, or the acid halide thereof, is reacted with ammonia to form the carbonamide which is in turn dehydrated to the nitrile by treatment with a dehydrating agent such as phosphorus pentoxide, thionyl chloride, etc. The nitrile is then treated with an azide, especially an alkali metal azide such as sodium or lithium azide, or ammonium azide in the presence of ammonium chloride or a Lewis acid such as aluminium chloride to form the 1H-tetrazolyl grouping. Such carbonamide and nitrile derivatives are also of interest as active compounds and constitute a further feature of the invention.

Compounds of formula I in which A is a 1H-tetrazolylcarbamoyl group may be prepared by reaction of the free 2-carboxylic acid with 5-amino-tetrazole in the presence of a dehydrating agent such as dicyclohexylcarbodiimide.

Starting materials of formula III may be prepared from starting materials of formula II by reaction with an oxidizing agent, particularly by reaction with sulfuryl chloride in an inert solvent such as a chlorinated hydrocarbon.

The starting materials of formula II may be prepared as in German Pat. Nos. 2,234,250 and 2,234,255. They may also be prepared by the cyclization of a compound of formula V

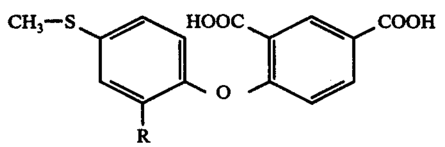

V wherein R is as hereinbefore defined in the presence of a strong acid to form a compound of formula VI

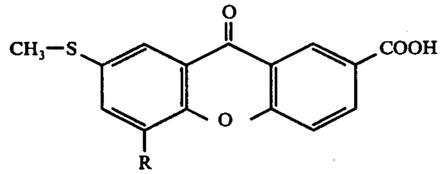

VI wherein R is as defined above, followed by esterification with an alcohol AlkOH wherein Alk is as defined hereinabove. A convenient strong acid for the cyclization is polyphosphoric acid or concentrated sulfuric acid. The esterification is conveniently effected under acid conditions such as by using sulfuric acid.

The compounds of formula V may be prepared from compounds of formula VII

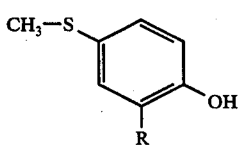

VII wherein R is as defined above by reaction with a diloweralkyl -4-haloisophthalate in the presence of mild base such as potassium carbonate and copper metal preferably in powder form, and preferably at elevated temperature. When the reaction has been completed, the reaction mixture may be warmed in the presence of base, such as an alkali metal hydroxide such as sodium or potassium hydroxide, to hydrolyze the diloweralkyl ester of the compound of formula V formed initially.

The compounds of formula VII may be prepared from compounds of formula VIII

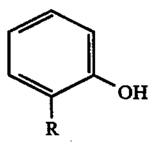

VIII wherein R is as hereinabove defined, by reaction thereof at room temperature with phosphorus oxychloride in perchloric acid in the presence of dimethyl sulfoxide. The initial product is in the sulfonium form as a perchlorate salt. The sulfide form may readily be formed however, for example, by refluxing the product in a concentrated aqueous salt solution such as saturated aqueous potassium chloride.

In the case where R is an alkoxy group, a mixture of 1-alkoxy-2-hydroxy-4-methylthio- and 1-alkoxy-2-hydroxy-5-methylthio-isomers is formed from which the desired 1-alkoxy -2-hydroxy-5-methylthio compound may be isolated by crystallization such as from an alkanol like ethanol.

The compounds of formula VIII may be prepared by the following routes:

a. when R is an alkoxy group of 1–9 carbon atoms, the compounds of formula VIII may be prepared by reaction of 1,2-dihydroxybenzene with a $C_1$ to $C_9$ alkyl halide, preferably bromide, in the presence of base, for example alkali metal hydroxide or alkoxide such as sodium hydroxide or ethoxide.

b. when R is an alkyl group of 2–9 carbon atoms, the compounds of formula VIII may be prepared by treatment of phenol with a $C_2$ to $C_9$ alkanoyl halide such as a chloride at ambient temperature. After isolation and purification of the phenyl ester, this may be heated in the presence of a Lewis acid, preferably aluminum trichloride to form a 2-hydroxyphenyl-($C_1$ to $C_8$ alkyl) ketone which, after isolation and purification by conventional means is reduced by a reagent reducing a carbonyl group to $-CH_2-$ such as by treatment with acidified zinc amalgam to form a 2-alkyl phenol. The compound of formula VIII in which R is methyl is a known substance.

The novel antiallergic compositions of the invention are comprised of an effective amount of at least one compound of formula I and a pharmaceutical carrier. The composition may be in the form of tablets, coated tablets, capsules, granules, solutions, syrups, sprays for application to the membranes of the bronchi throat, suppositories or injectable solutions or suspensions prepared in the usual manner.

Examples of suitable pharmaceutical carriers are talc, gum arabic, lactose, starch, magnesium stearate, cacao butter, animal and vegetable fats, paraffinic derivatives, glycols, propellants and various wetting agents, dispersants, emulsifiers, flavoring agents and preservatives.

The compositions because of their antiallergic activity are useful for the treatment of allergic asthma and asthmatiform bronchitis of allergic origin.

The novel method of the invention for relieving allergic symptoms comprises administering to warm-blooded animals including humans an antiallergically effective amount of at least one compound of formula I. The compounds may be administered parenterally, rectally, topically or orally. The usual daily dose is 0.01 to 2 mg/kg depending upon the method of administration.

In the following examples there are described several preferred embodiments to illustrate the invention. However, it is to be understood that the invention is not intended to be limited to the specific embodiments.

EXAMPLE 1

Methyl 7-(S-methylsulfonimidoyl)-xanthone-2-carboxylate

STEP A: Methyl 7-(methylsulfinyl)-xanthone-2-carboxylate

A solution of 50 g (0.167 mole) of methyl 7-(methylthio)-xanthone-2-carboxylate in 1000 ml of dichloromethane was cooled to about −50° C and then a solution of 20 ml (0.245 mole) of chlorosulfuric acid in 25 ml of dichloromethane was added thereto over 30 minutes while keeping the temperature at about −40° C. The reaction mixture was stirred for 3 hours at −40° C and then 100 ml of ethanol were added. The temperature of the mixture returned to room temperature and the mixture was washed with sodium carbonate solution and then water, was dried over magnesium sulfate and evaporated to dryness to 48.9 g of methyl 7-(methylsulfinyl)-xanthone-2-carboxylate which was crystallized from a benzene-petroleum ether mixture to obtain off-white crystals.

IR Spectrum:

ester carbonyl at $1732cm^{-1}$; xanthone carbonyl at $1670cm^{-1}$ and >SO at $1056cm^{-1}$.

STEP B: Methyl 7-(S-methylsulfonimidoyl)-xanthone-2-carboxylate 28.4 g (0.09 mole) of finely powdered methyl 7-(methylsulfinyl)-xanthone-2-carboxylate were dissolved with stirring in 600 ml of polyphosphoric acid heated to 60° C and then 10 g (0.15 mole) of sodium azide were added thereto in 1 g bits over 4 hours. The reaction mixture was then poured over ice with stirring and was made neutral by the addition of 0.88 N ammonium hydroxide solution. The cold solution was filtered to obtain 26.4 g of product which was crystallized from a chloroform-methanol mixture to obtain methyl 7-(S-methylsulfonimidoyl)-xanthone-2-carboxylate in the form of pale brown crystals melting at 229°-231° C.

IR Spectrum:

=NH of sulfoximine at $3300cm^{-1}$; ester carbonyl at $1730cm^{-1}$; xanthone carbonyl at $1665cm^{-1}$; and —N=S=O at 1220, 1060 and $945cm^{-1}$.

Analysis: $C_{16}H_{13}NO_5S$ Calculated: %C 58.02%H 3.96%N 4.23%S 9.46 Found: 57.69 3.94 3.89 9.74

EXAMPLE 2

7-(S-methylsulfonimidoyl)-xanthone-2-carboxylic acid

A mixture of 3.3 g (0.01 mole) of methyl 7-(S-methylsulfonimidoyl)-xanthone-2-carboxylate in 100 ml of ethanol and 100 ml of 0.125 N sodium hydroxide solution was refluxed for 3 hours and was cooled and filtered. The pH of the filtrate was adjusted to 5 by addition of 0.1 N hydrochloric acid and the mixture was filtered to obtain 2.72 g of 7-(S-methylsulfonimidoyl)-xanthone-2-carboxylic acid in the form of off-white micro crystals melting at 285°-286° C.

IR Spectrum:

=NH of sulfoximine at $3210cm^{-1}$; acid carbonyl at $1700cm^{-1}$; xanthone carbonyl at $1667cm^{-1}$; and —N=S=O at 1225 and $1070cm^{-1}$ Analysis: $C_{15}H_{11}NO_5S$ Calculated: %C 56.79%H 3.49%N 4.41%S 10.08 Found: 56.52 3.57 4.18 10.12

EXAMPLE 3

Methyl 7-(N-acetyl-S-methylsulfonimidoyl)-xanthone-2-carboxylate 25 ml of acetic acid anhydride were added to a solution of 1 g of methyl 7-(S-methylsulfonimidoyl)-xanthone-2-carboxylate in 50 ml of pyridine and the resulting solution was heated overnight on a steam bath. The mixture was poured into water and was extracted with chloroform. The chloroform extracts were washed with dilute hydrochloric acid, then water, were dried over magnesium sulfate and evaporated to dryness under reduced pressure to obtain 0.78 g of pale yellow product which was crystallized from a chloroform-petroleum ether mixture to obtain methyl 7-(N-acetyl-S-methylsulfonimidoyl)-xanthone-2-carboxylate as crystals melting at 248°-249° C.

IR Spectrum:

ester carbonyl at $1720cm^{-1}$; xanthone carbonyl at $1665cm^{-1}$; imide carbonyl at $1650cm^{-1}$; and —N=S=O at 1230 and $1070cm^{-1}$.

EXAMPLE 4

7-(N-acetyl-S-methylsulfonimidoyl)-xanthone-2-carboxylic acid

Using the procedure of Example 2, 1 g of methyl 7-(N-acetyl-S-methylsulfonimidoyl)-xanthone-2-carboxylate was hydrolyzed to obtain 0.89 g of 7-(N-acetyl-S-methylsulfonimidoyl)-xanthone-2-carboxylic acid melting at 260°-264° C.

IR Spectrum:

bands at 1715, 1667, 1620, 1230 and $1070cm^{-1}$.

EXAMPLE 5

Methyl 7-(N-benzoyl-S-methylsulfonimidoyl)-xanthone-2-carboxylate 1.21 g (0.008 mole) of benzoyl chloride and a small amount of triethylamine were added to a solution of 1 g (0.003 mole) of methyl 7-(S-methylsulfonimidoyl)-xanthone-2-carboxylate in 50 ml of chloroform and the resulting solution was refluxed for 4 hours and then was poured into water. The chloroform phase was washed with sodium carbonate solution, dilute hydrochloric acid and then water, dried over magnesium sulfate and evaporated to dryness to obtain 760 mg of residue. The residue was crystallized from a chloroform-ethanol mixture to obtain methyl 7-(N-benzoyl-S-methylsulfonimidoyl)-xanthone-2-carboxylate as white crystals melting at 217°-221° C.

IR Spectrum:

ester carbonyl at $1715cm^{-1}$; xanthone carbonyl at $1667cm^{-1}$; imide carbonyl at $1635cm^{-1}$; and —N=S=O at 1230 and $1070cm^{-1}$.

Analysis: $C_{23}H_{17}NO_6S$ Calculated: %C 63.45%H 3.94%N 3.22%S 7.35 Found: 63.15 4.01 2.97 7.32

EXAMPLE 6

7-(N-benzoyl-S-methylsulfonimidoyl)-xanthone-2-carboxylic acid

Using the method of Example 2, 1 g of methyl 7-(N-benzoyl-S-methylsulfonimidoyl)-xanthone-2-carboxylate was hydrolyzed to obtain 0.74 g of 7-(N-benzoyl-S-methylsulfonimidoyl)-xanthone-2-carboxylic acid melting at 310°-313° C.

IR Spectrum:

Acid carbonyl at $1710cm^{-1}$; xanthone carbonyl at $1670cm^{-1}$; imide carbonyl at $1630cm^{-1}$; and —N=S=O at 1225 and $1070cm^{-1}$.

EXAMPLE 7

Methyl 7-[N-(p-toluenesulfonyl)-S-methylsulfonimidoyl]-xanthone-2-carboxylate 1.0 g (0.0052 mole) of p-toluene sulfonyl chloride was added to a solution of 1.65 g (0.005 mole) of methyl 7-(S-methylsulfonimidoyl)-xanthone-2-carboxylate in 30 ml of anhydrous pyridine and the solution was heated on a water bath for 10 minutes and then was allowed to stand overnight at room temperature. The reaction mixture was poured into cold dilute hydrochloric acid and the mixture was extracted with ethyl acetate. The organic extracts were washed with water, dried over magnesium sulfate and evaporated to dryness to obtain 2.01 g of product which was crystallized from a chloroform-methanol mixture to obtain methyl 7-[N-(p-toluenesulfonyl)-S-methylsulfonimidoyl]-xanthone-2-carboxylate melting at 224°-227° C.

IR Spectrum:

ester carbonyl at 1730cm$^{-1}$; xanthone carbonyl at 1670cm$^{-1}$.

Analysis: $C_{23}H_{19}NO_7S_2$ Calculated: %C 56.92%H 3.95%N 2.88 Found 56.81 3.89 3.03

EXAMPLE 8

7-[N-(p-toluenesulfonyl)-S-methylsulfonimidoyl]-xanthone-2-carboxylic acid

Using the procedure of Example 2, 0.95 g of methyl 7-[N-(p-toluenesulfonyl)-S-methylsulfonimidoyl]-xanthone-2-carboxylate was hydrolyzed to obtain 0.75 g of product which was crystallized from a chloroform-methanol mixture to obtain 7-[N-(p-toluenesulfonyl)-S-methylsulfonimidoyl]-xanthone-2-carboxylic acid melting at 276°-278° C.

IR Spectrum:

acid carbonyl at 1715cm$^{-1}$; xanthone carbonyl at 1670cm$^{-1}$.

Analysis: $C_{22}H_{17}NO_7S_2$ Calculated: %C 56.06%H 3.63%N 2.97%S 13.59 Found: 55.43 3.72 2.92 13.18

EXAMPLE 9

Methyl 7-[N-(N'-morpholinoacetyl)-S-methylsulfonimidoyl]-xanthone-2-carboxylate

STEP A: Methyl 7-(N-chloroacetyl-S-methylsulfonimidoyl)-xanthone-2-carboxylate

A mixture of 2.5 g (0.0075 mole) of methyl 7-(S-methylsulfonimidoyl)-xanthone-2-carboxylate in 80 ml of anhydrous dimethylformamide and 2.6 g (0.015 mole) of chloroacetic acid anhydride was stirred at room temperature for 3 hours and the mixture was then poured into water and extracted with chloroform. The chloroform extracts were washed with dilute hydrochloric acid and then water, dried over magnesium sulfate and evaporated to dryness. The 2.7 g of residue were crystallized from a chloroform-ethanol mixture to obtain methyl 7-(N-chloroacetyl-S-methylsulfonimidoyl)-xanthone-2-carboxylate as pale yellow crystals melting at 214°-216° C.

IR Spectrum:

ester carbonyl at 1720cm$^{-1}$; xanthone carbonyl and imide carbonyl at 1665cm$^{-1}$; and —N=S=O at 1225 and 1070cm$^{-1}$.

STEP B: Methyl 7-/N-(N'-morpholinoacetyl)-S-methylsulfonimidoyl/-xanthone-2-carboxylate.

A solution of 500 mg (0.0012 mole) of methyl 7-(N-chloroacetyl-S-methylsulfonimidoyl)-xanthone-2-carboxylate and 0.5 g (0.006 mole) of morpholine in dichloromethane was stirred at room temperature for 24 hours and was then poured into water. The dichloromethane phase was dried over magnesium sulfate and evaporated to dryness to obtain 480 mg of crude product. The latter was crystallized from a chloroform-methanol mixture to obtain pure methyl 7-[N-(N'-morpholinoacetyl)-S-methylsulfonimidoyl]-xanthone-2-carboxylate melting at 216°-219° C.

IR Spectrum:

ester carbonyl at 1730cm$^{-1}$; xanthone carbonyl and imide carbonyl at 1670cm$^{-1}$; and —N=S=O at 1220 and 1065cm$^{-1}$.

EXAMPLE 10

Methyl 7-[N-(α-piperidinoacetyl)-S-methylsulfonimidoyl]-xanthone-2-carboxylate

Using the procedure of Step B of Example 9, methyl 7-(N-chloromethyl-S-methylsulfonimidoyl)-xanthone-2-carboxylate and piperidine were reacted to obtain methyl 7-[N-(α-piperidinoacetyl)-S-methylsulfonimidoyl]-xanthone-2-carboxylate.

IR Spectrum:

ester carbonyl at 1720cm$^{-1}$; xanthone carbonyl at 1675cm$^{-1}$; imide carbonyl at 1660 cm$^{-1}$; and —N=S=O at 1215 and 1070cm$^{-1}$.

EXAMPLE 11

Methyl 7-(N-carbamoyl-S-methylsulfonimidoyl)-xanthone-2-carboxylate 1 g (0.015 mole) of sodium cyanate was added to a solution of 500 mg (0.0015 mole) of methyl 7-(S-methylsulfonimidoyl)-xanthone-2-carboxylate in 20 ml of acetic acid and the mixture was stirred overnight at room temperature and was then poured into water. The mixture was extracted with ethyl acetate and the organic extracts were washed with sodium bicarbonate solution and then water, dried over magnesium sulfate and evaporated to dryness. The 385 mg of residue was crystallized from a chloroform-methanol mixture to obtain pure methyl 7-(N-carbamoyl-S-methylsulfonimidoyl)-xanthone-2-carboxylate melting at 217°-220° C.

IR Spectrum:

amino at 3420cm$^{-1}$; ester carbonyl at 1725cm$^{-1}$; xanthone carbonyl at 1665cm$^{-1}$; and imide carbonyl at 1645cm$^{-1}$.

Analysis: $C_{17}H_{14}N_2O_6S$ Calculated: %C 54.55%H 3.77%N 7.48%S 8.55 Found: 54.24 3.73 7.31 8.59

EXAMPLE 12

7-(N-carbamoyl-S-methylsulfonimidoyl)-xanthone-2-carboxylic acid

Using the procedure of Example 2, 300 mg of methyl 7-(N-carbamoyl-S-methylsulfonimidoyl)-xanthone-2-carboxylate were hydrolyzed to obtain 235 mg of 7-(N-carbamoyl-S-methylsulfonimidoyl)-xanthone-2-carboxylic acid which when crystallized from a chloroform-dimethylformamide mixture melted at 277°-279° C.

IR Spectrum:

amino at 3470cm$^{-1}$; acid carbonyl at 1700cm$^{-1}$; xanthone carbonyl at 1665cm$^{-1}$ and imide carbonyl at 1645cm$^{-1}$.

Analysis: $C_{16}H_{12}N_2O_6S$ Calculated: %C 53.34%H 3.36%N 7.78%S 8.88 Found: 52.93 3.42 7.52 8.83

EXAMPLE 13

Methyl 7-[N-(2',2'-bisethoxycarbonyl)ethenyl-S-methylsulfonimidoyl]-xanthone-2-carboxylate A mixture of 4 g (0.012 mole) of methyl 7-(S-methylsulfonimidoyl)-xanthone-2-carboxylate and 35 ml of diethyl ethoxymethylmalonate was heated at 125° C for 24 hours and the reaction product was crystallized from an ethanol-chloroform mixture to obtain 3.05 g of methyl 7-[N-(2',2'-bisethoxycarbonyl)-ethenyl-S-methylsulfonimidoyl]-xanthone-2-carboxylate as a white crystalline solid melting at 225°-230° C.

IR Spectrum:

ester carbonyl at $1730cm^{-1}$ and xanthone carbonyl at $1680cm^{-1}$.

Analysis: $C_{24}H_{23}NO_9S$ Calculated: %C 57.49%H 4.59%N 2.79%S 6.39 Found: 57.03 4.48 2.59 6.29

EXAMPLE 14

Methyl 7-[N-(p-toluenesulfonyl)-S-methylsulfimidoyl]-xanthone-2-carboxylate

A mixture of 1.2 g (0.004 mole) of methyl 7-(methylthio)-xanthone-2-carboxylate and 1.2 g (0.0043 mole) of chloramine T [sodium p-toluenesulfonyl chloroamide] in 100 ml of a 2-1 dioxane-water mixture was refluxed for 1 hour and then held overnight at 0° C. The mixture was filtered to obtain 1.0 g of crystalline methyl 7-[N-(p-toluenesulfonyl)-S-methyl-sulfonimidoyl]-xanthone-2-carboxylate melting at 226°-229° C.

IR Spectrum:

ester carbonyl at $1720cm^{-1}$; xanthone carbonyl at $1675cm^{-1}$; $—SO_2—$ at 1280 and $1140cm^{-1}$ and >S=N— at $955cm^{-1}$.

Analysis: $C_{23}H_{19}NO_6S_2$ Calculated: %C 58.85%H 4.08%N 2.98%S 13.63 Found: 58.50 4.10 2.62 13.23

EXAMPLE 15

7-/N-(p-toluenesulfonyl)-S-methylsulfimidoyl/-xanthone-2-carboxylic acid

Using the procedure of Example 2, 085 g (0.0018 mole) of methyl 7-[N-(p-toluenesulfonyl)-S-methylsulfimidoyl]-xanthone-2-carboxylate was hydrolyzed to obtain 0.69 g of 7-[N-(p-toluenesulfonyl)-S-methylsulfimidoyl]-xanthone-2-carboxylic acid as a white crystalline solid melting at 330° C (decomp.).

IR Spectrum:

acid carbonyl at $1695cm^{-1}$; xanthone carbonyl at $1680cm^{-1}$; $—SO_2—$ at 1290 and $1140cm^{-1}$ and >S=N—at $950cm^{-1}$.

EXAMPLE 16

Methyl 7-(S-methylsulfonimidoyl)-5-(n-hexyl)-xanthone-2-carboxylate

STEP A: Phenyl hexanoate 30 ml (0.22 mole) of hexanoyl chloride were added dropwise over 30 minutes with stirring and cooling on an ice bath to a solution of 18.8 g (0.2 mole) of phenol in 80 ml of anhydrous pyridine and then the reaction mixture stood at room temperature for 3 hours and was poured into ice water. The mixture was extracted with ether and the ether extracts were washed with water, dilute hydrochloric acid and with water, dried over magnesium sulfate and evaporated to dryness to obtain 36.4 g of phenyl hexanoate as a yellow oil.

STEP B: 1-(2'-hydroxyphenyl)-hexan-1-one 24 g (0.18 mole) of powdered aluminium trichloride were carefully added to 31 g (0.16 mole) of phenyl hexanoate and the mixture was slowly heated with occassional stirring to 120° C and was held there for 1½ hours. The residue was ground into a powder and was poured into iced dilute hydrochloric acid with stirring. The mixture was extracted with ether and the ether extracts were washed with dilute sodium hydroxide solution, then with water, dried over magnesium sulfate and evaporated to dryness to obtain 14.2 g of (1-(2'-hydroxyphenyl)-hexan-1-one as a pale yellow oil. IR spectrum showed o-hydroxyphenylcarbonyl at $1650cm^{-1}$.

STEP C: 2-(n-hexyl)-phenyl 40 g (0.61 mole) of powdered zinc was admixed with a solution of 0.8 g (0.003 mole) of mercuric chloride in 60 ml of water and the mixture was allowed to stand with occassional skaking for half an hour. The supernatant liquid was poured off and the zinc amalgam was washed once with water. 80 ml of 6 N hydrochloric acid and then a solution of 12.8 g (0.067 mole) of the 1-(2'-hydroxyphenyl-hexan-1-one in 20 ml of ethanol were added to the zinc amalgam and the mixture was refluxed with stirring for 6 hours until the reaction was complete. The mixture was poured into water and the mixture was extracted with ether. The ether extracts were twice washed with water, dried over magnesium sulfate and evaporated to dryness to obtain 7.6 g of crude 2-(n-hexyl)-phenol which was distilled to obtain a pure fraction at a boiling point of 103° to 105° C at 0.8 mm Hg as a colorless oil. The IR Spectrum showed a hydroxy at $3420cm^{-1}$. Dissolution of the metallic residues in concentrated hydrochloric acid and extraction thereof with ether yielded another 2.9 g of crude 2-(n-hexyl)-phenol.

STEP D: 4-methylthio-2-(n-hexyl)-phenol 7.1 g (0.04 mole) of 2-(n-hexyl)-phenol were added to a cooled, stirring solution of 16 ml of phosphorus oxychloride in 20 ml of 70% perchloric acid and then 2.8 ml (0.04 mole) of dimethylsulfoxide were added dropwise thereto at a temperature of 25° C. After the addition, the reaction temperature was returned to room temperature with continued stirring and after 3 hours, the mixture was poured onto ice. The mixture was extracted with ethyl acetate and the ethyl acetate extract was washed twice with water, with sodium bicarbonate solution and then water, dried over magnesium sulfate and evaporated to dryness to obtain 11.8 g of crude 4-dimethylsulfonium-2-(n-hexyl)-phenol perchlorate as a brown gum.

A mixture of 11.5 g of the said perchlorate in 200 ml of a saturated potassium chloride solution was refluxed for 4 hours and after cooling, the mixture was extracted with ether. The ether extracts were washed with water, dried over magnesium sulfate and evaporated to dryness to obtain 7.1 g of 4-methylthio-2-(n-hexyl)-phenol as a yellow oil. The IR spectrum showed a hydroxyl at $3320cm^{-1}$. The oil crystallized on standing and after crystallization from petroleum ether (b.p. −40° to 60° C) had a melting point of 42°-44° C.

STEP E: 4-[4'-methylthio-2'-(n-hexyl)-phenoxy]-isophthalic acid 0.4 g of copper powder and 5.5 g (0.04 mole) of potassium carbonate were added to a solution of 5.5 g (0.02 mole) of dimethyl 4-bromoisophthalate and 4.5 g (0.02 mole) of 4-methylthio-2-(n-hexyl)-phenol in 40 ml of nitrobenzene and the mixture was heated under a nitrogen atmosphere at 140° C for 3 hours and then was cooled. A solution of 3.2 g (0.08 mole) of sodium hydroxide in 60 ml of a 3-1 ethanol-water mixture was added thereto and the mixture was refluxed for 1 hour and then was poured into ice water. The mixture was extracted 3 times with dichloromethane and the aqueous phase was acidified with dilute hydrochloric acid and was filtered. The recovered solid was crystallized from methanol to obtain 5.8 g of 4-[4'-methylthio-2'-(n-hexyl)-phenoxy]-isophthalic acid.

STEP F: 7-methylthio-5-(n-hexyl)-xanthone-2-carboxylic acid 40 ml of polyphosphoric acid were added to a solution of 3.9 g (0.01 mole) of 4-[4'-methylthio-2'-(n-hexyl)-phenoxy]-isophthalic acid in 40 ml of sulfolane and the mixture was stirred for 1 hour, iced and poured into water. The mixture was filtered and the solid precipitate was washed with water and crystallized from ethanol to obtain 2.8 g of 7-methylthio-5-(n-hexyl)-xanthone-2-carboxylic acid melting at 164°-170° C. The IR spectrum showed a carboxyl at $1692cm^{-1}$ and xanthone carbonyl at $1665cm^{-1}$.

STEP G: methyl 7-methylthio-5-(n-hexyl)-xanthone-2-carboxylate

A solution of 2.0 g of 7-methylthio-5-(n-hexyl)-xanthone-2-carboxylic acid in 2 ml of concentrated sulfuric acid and 40 ml of methanol was refluxed for 3 hours and was then poured into water. The mixture was extracted with chloroform and the chloroform extracts were washed with sodium bicarbonate solution and then water, dried over magnesium sulfate and evaporated to dryness. The 2 g of gummy residue were crystallized from petroleum ether (b.p. −40°-60° C) to obtain methyl 7-methylthio-5-(n-hexyl)-xanthone-2-carboxylate as pale yellow crystals melting at 63°-64° C.

Analysis: $C_{22}H_{24}O_4S$ Calculated: %C 68.74 %H 6.29 %S 8.32 Found: 68.51 6.42 8.37

STEP H: methyl 7-methylsulfinyl-5-(n-hexyl)-xanthone-2-carboxylate 0.4 ml (0.0044 mole) of chlorosulfuric acid were added dropwise with stirring to a solution of 1.5 g (0.004 mole) of methyl 7-methylthio-5-(n-hexyl)-xanthone-2-carboxylate in 150 ml of dichloromethane cooled to −50° C and the temperature was held at −50° to −40° C for 2 hours after which 5 ml of ethanol were added. The reaction mixture temperature was raised to room temperature and the mixture was washed with sodium bicarbonate solution and then water, dried over magnesium sulfate and evaporated to dryness. The pale yellow solid residue was crystallized from methanol to obtain 1.0 g of methyl 7-methylsulfinyl-5-(n-hexyl)-xanthone-2-carboxylate melting at 130°-132° C.

IR Spectrum:

$-COOCH_3$ at $1725cm^{-1}$; xanthone carbonyl at $1670cm^{-1}$; and sulfoxide at $1060cm^{-1}$.

STEP I: methyl 7-(S-methylsulfonimidoyl)-5-(n-hexyl)-xanthone-2-carboxylate 0.16 g (0.0025 mole) of sodium azide was added in small portions with stirring to a solution of 0.8 g (0.002 mole) of methyl 7-methylsulfinyl-5-(n-hexyl)-xanthone-2-carboxylate in 80 ml of polyphosphoric acid at 45°-50° C and stirring was continued for 1 hour after which the mixture was poured onto ice. The reaction mixture was neutralized with 0.88 N ammonium hydroxide solution and was then extracted with ethyl acetate. The ethyl acetate extracts were washed with water, dried over magnesium sulfate and evaporated to dryness. The 0.74 g of yellow-brown solid residue was crystallized from methanol to obtain 0.44 g of methyl 7-(S-methylsulfonimidoyl)-5-(n-hexyl)-xanthone-2-carboxylate as an off-white solid.

EXAMPLE 17

7-(S-methylsulfonimidoyl)-5-(n-hexyl)-xanthone-2-carboxylic acid 5.5 ml of an 0.1 N sodium hydroxide solution was added to a solution of 0.208 g (0.005 mole) of methyl 7-(S-methylsulfonimidoyl)-5-(n-hexyl)-xanthone-2-carboxylate in 5 ml of ethanol and the solution was refluxed for 1 hour and poured onto ice. The mixture was acidified with dilute hydrochloric acid and was filtered. The recovered precipitate was washed with water and dried to obtain 0.182 g of 7-(S-methylsulfonimidoyl)-5-(n-hexyl)-xanthone-2-carboxylic acid melting at 193°-194° C.

IR Spectrum: =NH at $3260cm^{-1}$; carboxyl at 1715cm−1 and xanthone carbonyl at $1678cm^{-1}$.

EXAMPLE 18

7-(N-carbamoyl-S-methylsulfonimidoyl)-5-(n-hexyl)-xanthone-2-carboxylic acid Step A: methyl 7-(N-carbamoyl-S-methylsulfonimidoyl)-5-(n-hexyl)-xanthone-2-carboxylate 0.10 g (0.0015 mole) of sodium cyanate were added to a solution of 104 mg (0.0025 mole) of methyl 7-(S-methylsulfonimidoyl)-5-(n-hexyl)-xanthone-2-carboxylate in 5 ml of glacial acetic acid and the mixture was stirred at room temperature for 10 hours and was then poured into water. The mixture was extracted with ethyl eter and the ethyl acetate extracts were washed with sodium bicarbonate solution, then water, dried over magnesium sulfate and evaporated to dryness. The residue was triturated with ethanol to obtain 78 mg of methyl 7-(N-carbamoyl-S-methylsulfonimidoyl)-5-(n-hexyl)-xanthone-2-carboxylate in the form of a white solid.

IR Spectrum: $-NH_2$ at 3440 and $3195cm^{-1}$; $-COOCH_3$ at $1728cm^{-1}$; and $-CONH_2$ at $1670cm^{-1}$.

STEP B: 7-(N-carbamoyl-S-methylsulfonimidoyl)-5-(n-hexyl)-xanthone-2-carboxylic acid Using the procedure of Example 2, 80 mg of methyl 7-(N-carbamoyl-S-methylsulfonimidoyl)-5-(n-hexyl)-xanthone-2-carboxylate were hydrolyzed to obtain 58 mg of 7-(N-carbamoyl-S-methylsulfonimidoyl)-5-(n-hexyl)-xanthone-2-carboxylic acid melting at 214°-216° C.

IR Spectrum:

$-NH_2$ at 3460 and $3220cm^{-1}$; carboxyl at $1700cm^{-1}$ and $-CONH_2$ at $1675cm^{-1}$.

EXAMPLE 19

Methyl 7-(S-methylsulfonimidoyl)-5-(n-pentyloxy)-xanthone-2-carboxylate

STEP A: 2-(n-pentyloxy)-phenol 110 g (1 mole) of catechol was added to a solution of 23 g (1 mole) of metallic sodium in 1 liter of absolute ethanol and the mixture was stirred under nitrogen for 1 hour. Then, 166 g ((1.1 mole) of 1-bromopentane were added dropwise to the mixture over 15 minutes and the mixture was refluxed with stirring for 3 hours, was cooled and poured into 3 liters of water. The mixture was extracted with 1000 ml of ether and the ether extracts were washed with 20% sodium carbonate solution and then water, dried over magnesium sulfate and evporated to dryness under reduced pressure to obtain 157 g of 2-(n-pentyloxy)-phenol as a yellow oil. IR spectrum showed OH at $3540cm^{-1}$.

STEP B: 4-methylthio-2-(n-pentyloxy)-phenol 5.4 g (0.03 mole) of 2-(n-pentyloxy)-phenol were added to a cooled solution of 12 ml of phosphoryl chloride in 15 ml of 70% perchloric acid and after cooling the resulting solution to −20° C, 2.34 g (0.03 mole) of dimethylsulfoxide were added thereto dropwise with stirring while keeping the temperature at −20° to −15° C. After the addition, the mixture was stirred at −20° C for one hour and after raising the temperature to room temperature, the mixture was stirred for another 3 hours. The mixture was then poured into ice water and was extracted with ethyl acetate. The ethyl acetate extracts were washed with 100 ml of water, 100 ml of 5% sodium bicarbonate solution and 50 ml of water, dried over magnesium sulfate and evaporated to dryness under reduced pressure to obtain from 3 runs a total of 27.4g of 4-dimethylsulfonium-2-(n-pentyloxy)-phenol and 5-dimethylsulfonium-2-(n-pentyloxy)-phenol perchlorates as a viscous brown oil.

The said product in 300 ml of a saturated potassium chloride solution was refluxed for 4 hours and after cooling, the mixture was extracted with ether. The ether extracts were washed with water, dried over magnesium sulfate and evaporated to dryness under reduced pressure to obtain 17.6 g of a mixture of 4-methylthio-2-(n-pentyloxy)-phenol and 5-methylthio-2-(n-pentyloxy)-phenol in the form of a brown oil. The mixture was crystallized from ethanol at $-70°$ C to obtain 6.8 g of a mixture containing 80% of the 4-methylthio isomer compared to 66% in the original mixture (NMR determination). A second crystallization at $-70°$ C gave 3.7 g of 4-methylthio-2-(n-pentyloxy)-phenol showing no impurity by NMR in the form of white needles melting at 35°-36° C. The IR spectrum showed a hydroxyl at $3420cm^{-1}$.

STEP C: 4-[4'-methylthio-2'-(n-pentyloxy)-phenoxy]-isophthalic acid 4.40 g (0.032 mole) of anhydrous potassium carbonate and then 0.16 g of powdered copper were added to a solution of 3.60 g (0.016 mole) of 4-methylthio-2-(n-pentyloxy)-phenol and 4.37 g (0.016 mole) of dimethyl 4-bromo-isophthalate in 40 ml of nitrobenzene and the mixture was heated with stirring at 120° C under nitrogen for 3 hours. After cooling the mixture to 100° C, a solution of 1.92 g of sodium hydroxide pellets in 50 ml of a 1—1 ethanol-water mixture was added thereto and the mixture was refluxed for one hour. The mixture was cooled and 100 ml of water were added. The mixture was extracted with 100 ml of ether and the aqueous layer was washed twice with 50 ml of ether and was then acidified with 10% hydrochloric acid. The mixture was extracted with ether and the ether extract was washed with water, dried over magnesium sulfate and evaporated to dryness under reduced pressure to obtain an off-white solid residue. The residue was triturated with petroleum ether to obtain 5.3 g of 4-[4'-methylthio-2'-(n-pentyloxy)-phenoxy]-isophthalic acid. The IR spectrum showed a bonded hydroxy at 3500 to $2200cm^{-1}$ and carboxyl at $1700cm^{-1}$.

STEP D: 7-methylthio-5-(n-pentyloxy)-xanthone-2-carboxylic acid 50 ml of polyphosphoric acid were added to a solution of 5.3 g of 4-]4'-methylthio-2'-(n-pentyloxy)-phenoxy]-isophthalic acid in 50 ml of sulfolane and after heating for 2 hours at 110° C, the mixture was carefully poured into ice water. The mixture was extracted with ether and the ether extracts were washed with water, dried over magnesium sulfate and evaporated to dryness under reduced pressure to obtain a yellow gummy residue. The residue was triturated with ether to obtain 1.5 g of 7-methylthio-5-(n-pentyloxy)-xanthone-2-carboxylic acid melting at 205°-208° C.

IR Spectrum:

bonded OH at 3300-$2300cm^{-1}$; carboxyl at $1700cm^{-1}$; and xanthone carbonyl at $1665cm^{-1}$.

STEP E : methyl 7-methylthio-5-(n-pentyloxy)-xanthone-2-carboxylate 1 ml of concentrated sulfuric acid was carefully added to a suspension of 2 g of 7-methylthio-5-(n-pentyloxy)-xanthone-2-carboxylic acid in 100 ml of methanol and the mixture was warmed until the solids dissolved and was then refluxed for 18 hours. The cooled solution was concentrated by evaporation under reduced pressure and was then poured into 200 ml of water. The mixture was extracted with ether and the ether extracts were washed with water, dried over magnesium sulfate and evaporated to dryness under reduced pressure to obtain a yellow oil which was triturated with methanol. The resulting solid was crystallized from methanol to obtain 1.8 g of methyl 7-methylthio-5-(n-pentyloxy)-xanthone-2-carboxylate as yellow needles melting at 116°-118° C. The IR spectrum showed $—COOCH_3$ at $1730cm^{-1}$ and xanthone carbonyl at $1660cm^{-1}$ Analysis: $C_{21}H_{22}O_5S$ Calculated: %C 65.27 %H 5.74 %S 8.30 Found: 65.37 5.81 8.36

STEP F: Methyl 7-methylsulfinyl-5-(n-pentyloxy)-xanthone-2-carboxylate

A solution of 0.45 ml (5.5 mmol) of sulfonyl chloride in 10 ml of methylene chloride was added dropwise with stirring to a solution of 1.70 g (4.4 mmol) of methyl 7-methylthio-5-(n-pentyloxy)-xanthone-2-carboxylate in 40 ml of methylene chloride cooled to $-45°$ C and after stirring for 2 hours at $-40°$ C, 25 ml of ethanol were added thereto. The reaction temperature was raised to room temperature and the solution was washed twice with 50 ml of 10% sodium carbonate solution, then water, dried over magnesium sulfate and evaporated to dryness. The yellow oil residue was triturated with methanol and the resulting solid was crystallized from methanol to obtain 1.35 g of methyl 7-methylsulfinyl-5-(n-pentyloxy)-xanthone-2-carboxylate as pale yellow crystals melting at 164°-165° C.

IR Spectrum:

$—COOCH_3$ at $1730cm^{-1}$; xanthone carbonyl at $1680cm^{-1}$; and sulfoxide at $1050cm^{-1}$.

Analysis: $C_{21}H_{22}O_6S$ Calculated: %C 62.67 %H 5.51 %S 7.97 Found: 62.57 5.56 7.94

STEP G: methyl 7-(S-methylsulfonimidoyl)-5-(n-pentyloxy)-xanthone-2-carboxylate 98 mg (1.5 mmol) of sodium azide were added with stirring in small amounts to a deep red solution of 0.4 g (1 mmol) of methyl 7-(methylsulfinyl)-5-(n-pentyloxy)-xanthone-2-carboxylate in polyphosphoric acid at 50° C and the mixture was stirred for one hour at 50° C and then cooled. The mixture was poured into ice water and was made alkaline by addition of 0.88 N ammonium hydroxide solution. The mixture was extracted with ethyl acetate and the ethyl acetate extracts were washed with water, dried over magnesium sulfate and evaporated to dryness. The brown oil residue was triturated with ethyl acetate to obtain 0.11 g of methyl 7-(S-methylsulfonimidoyl)-5-(n-pentyloxy)-xanthone-2-carboxylate in the form of white crystals.

IR Spectrum:

$=NH$ at $3290cm^{-1}$; $—COOCH_3$ at $1730cm^{-1}$; and xanthone carbonyl at $1665cm^{-1}$.

In another method, 108 mg (0.5 mmole) of O-mesitylene sulfonyl hydroxylamine were added to a solution of 100 mg (0.25 mmole) of methyl 7-(methylsulfinyl)-5-(n-pentyloxy)-xanthone-2-carboxylate in 10 ml of dichloromethane and the solution was stirred at room temperature for 2 days after which only a trace of sulfoxide remained. The mixture was poured into 25 ml of 10% sodium hydroxide solution and after stirring for 10 minutes, the organic layer was removed. The aqueous layer was extracted twice with dichloromethane and the combined extracts were dried over magnesium sulfate and evaporated to dryness to obtain an oil residue which was triturated with ethyl acetate to obtain 51 mg of methyl 7-(S-methylsulfonimidoyl)-5-(n-pentyloxy)-xanthone-2-carboxylate as white crystals.

EXAMPLE 20

7-(S-methylsulfonimidoyl)-5-(n-pentyloxy)-xanthone-2-carboxylic acid

Using the procedure of Example 2, 125 mg of methyl 7-(S-methylsulfonimidoyl)-5-(n-pentyloxy)-xanthone-2-carboxylate were hydrolyzed to obtain 91 mg of 7-(S-methylsulfonimidoyl)-5-(n-pentyloxy)-xanthone-2-carboxylic acid as an off-white solid melting at 253°-255° C.

IR Spectrum:

bonded OH at 3600-2300cm$^{-1}$; carboxyl at 1695cm$^{-1}$; and xanthone carbonyl at 1670cm$^{-1}$; N-H at 3300cm$^{1.}$

EXAMPLE 21

Tris(hydroxymethyl)methylamine salt of 7-(S-methylsulfonimidoyl)-5-(n-hexyl)-xanthone-2-carboxylic acid A solution of 1.33 g of tris(hydroxymethyl)methylamine in 3 ml of water was added to a solution of 4 g of 7-(S-methylsulfonimidoyl)-5-(n-hexyl)-xanthone-2-carboxylic acid in 50 ml of ethanol and the resulting solution was reduced to a volume of about 20 ml by evaporation under reduced pressure and was cooled to 0° C. The mixture was filtered and the recovered crystalline solid was washed with cold ethanol to obtain 4.69 g of the tris(hydroxylmethyl)methylamine salt of 7-(S-methylsulfonimidoyl)-5-(n-hexyl)-xanthone-2-carboxylic acid melting at 154°-160° C.

IR Spectrum:

hydroxyl at 3420cm$^{-1}$; xanthone carbonyl at 1675cm$^{-1}$; and carboxylate at 1625 and 1380cm$^{-1}$.

EXAMPLE 22

Sodium 7-(S-methylsulfonimidoyl)-5-(n-hexyl)-xanthone-2-carboxylate

A solution of 440 mg of sodium hydroxide in 2.75 ml of water was added to a solution of 4 g of 7-(S-methylsulfonimidoyl)-5-(n-hexyl)-xanthone-2-carboxylic acid in 50 ml of ethanol and after reducing the volume of the mixture to about 15 ml by evaporation under reduced pressure, the mixture was cooled to 0° C and filtered. The recovered crystalline solid was washed with cold ethanol to obtain 3.87 g of the sodium salt of the said acid melting at 192°-195° C. The infrared spectrum showed the xanthone carbonyl at 1670cm$^{-1}$ and a carboxylate at 1628 and 1380cm$^{-1}$.

PHARMACOLOGICAL EXAMPLES

EXAMPLE A

Tablets were prepared containing 2 mg of 7-(S-methylsulfonimidoyl)-xanthone-2-carboxylic acid and sufficient excipient comprised of lactose, talc, starch and magnesium stearate for 1 tablet.

EXAMPLE B

Capsules were filled with a mixture of 2 mg of 7-(S-methylsulfonimidoyl)-xanthone-2-carboxylic acid and sufficient lactose to fill a 30 mg capsule.

EXAMPLE C

Capsules were filled with a mixture of 2 mg of methyl 7-(N-acetyl-S-methylsulfonimidoyl)-xanthone-2-carboxylate and sufficient lactose to fill a 30 mg capsule.

EXAMPLE D

A metered dose aerosol dispenser was packed with the following ingredients per dose: 2 mg of 7-(S-methylsulfonimidoyl)-xanthone-2-carboxylic acid, 0.07 mg of emsulsifier and 50 mg of propellant.

EXAMPLE E

Tablets were prepared containing 2 mg of the sodium salt of 7-(S-methylsulfonimidoyl)-5-(n-hexyl)-xanthone-2-carboxylic acid and sufficient excipient comprised of lactose, talc, starch, and magnesium stearate for 1 tablet.

EXAMPLE F

Tablets were prepared containing 2 mg of the sodium salt of 7-(N-carbamoyl-S-methylsulfonimidoyl)-5-(n-hexyl)-xanthone-2-carboxylic acid and sufficient excipient comprised of lactose, talc, starch and magnesium stearate for 1 tablet.

EXAMPLE G

Tablets were prepared containing 2 mg of the sodium salt of 7-(S-methylsulfonimidoyl)-5-(n-pentyloxy)-xanthone-2-carboxylic acid and sufficient excipient comprised of lactose, talc, starch and magnesium stearate for 1 tablet.

PHARMACOLOGICAL STUDY

Anti-Allergic Activity

The anti-allergic activity of the products of the invention was determined by the method of Ovary [Passive Cutaneous Anaphylaxis in Allergology (1962), p. 358-67 Pergamon Press] in which cutaneous anaphylaxis was induced in rats by intradermal (ID) sensitization with antiserum followed 3 days later by systemic challenge with antigen. Evans blue dye was injected with the antigen to act as a marker to assess the severity of the local response which is inhibited by anti-allergic compounds. Groups of 7 male rats weighing 180 to 220 g. were used in this test.

Preparation of antigen for sensitization (such as alum precipitated ovalbumin) was effected by washing 120 grams of $Al(OH)_3$ gel in 140 mls of saline solution (use of a macerator facilitates mixing). Then, the product was centrifuged at 3,000 r.p.m. for about 10 minutes and the precipitate was responded with 300 mls of albumin egg powder (1.3 mg/ml) in saline solution and allowed to stand for 30 minutes. Then, the mixture was centrifuged at 3,000 r.p.m. for 10 minutes and the wet precipitate was weighed and to each gram weight 1 ml of saline solution was added. The antigen was stored in the refrigerator and was a quantity sufficient for 60 rats for a 3 day sensitization program.

Preparation of antiserum (such as anti-ovalbumin) was effected by injecting 1 ml of the alum precipitated ovalbumin subcutaneously into the rats on days 0, 2 and 4. The rats were bled on day 14 either by cardiac puncture or via the dorsal abdominal aorta and equal quantities of serum from each animal were pooled and thoroughly mixed. 2 ml aliquots were stored at −20° C in plastic tubes. The antiserum for sensitization was diluted so that an ID injection of 0.1 ml into control animals gave an average score of a single spot of between 2.0–3.5 using a 4 point scoring system.

For sensitization, rats were anaesthetized with Nembutal (40–60 mg/kg i.p.) and were then sensitized by four ID injections (0.1 ml each) on their shaved backs. The animals were then left for a period of three days to develope sensitization.

For the challenge, the sensitized rats were anaesthetized and challenged intravenously via the superficial penile vein with the anti-allergic compound, followed immediately by 1 ml of an antigen/Evans blue mixture (1 mg albumin egg powder in 0.5 ml saline solution plus 0.5 ml of 1% Evans blue). The injections were speeded up by using an automatic 1 ml self filling glass syringe. The "challenged" rats were killed after 30 minutes and their skin on the dorsal surface was removed. The degree and area of blueing, proportional to the anaphylactic reaction, was assessed on a four point scoring system as follows:

Calculations

1. Total scores for sites, 1,2,3 and 4 = X
2. Mean value of X for each group = $\bar{X}$
3. $\bar{X}t$ = $\bar{X}$ for test group
   $\bar{X}c$ = $\bar{X}$ for control group
4. % inhibition = ($\bar{X}c$ − $\bar{X}t/\bar{X}c$) × (100/1)
5. $ED_{50}$ = dose of drug giving 50% inhibition The results are reported in Table I and it should be noted that compounds listed in the Table were used in the form of their tris(hydroxymethyl) methylamine salts.

TABLE I

| Test Compound | $ED_{50}$ in mg/kg |
|---|---|
| 7-(S-methylsulfonimidoyl)-xanthone-2-carboxylic acid | 0.033 |
| 7-(N-acetyl-S-methylsulfonimidoyl)-xanthone-2-carboxylic acid | 0.065 |
| 7-(N-benzoyl-S-methylsulfonimidoyl)-xanthone-2-carboxylic acid | 0.68 |
| 7-[N-(p-toluenesulfonyl)-S-methylsulfimidoyl]-xanthone-2-carboxylic acid | 0.43 |
| 7-(S-methylsulfonimidoyl)-5-(n-hexyl)-xanthone-2-carboxylic acid | 0.0028 |
| 7-(N-carbamoyl-S-methylsulfonimidoyl)-5-(n-hexyl)-xanthone-2-carboxylic acid | 0.0080 |
| 7-(S-methylsulfonimidoyl)-5-(n-pentyloxy)-xanthone-2-carboxylic acid | 0.0035 |

The results of Table I show that compounds of the invention possess anti-allergic activity.

Various modifications of the products and methods of the invention may be made without departing from the spirit or scope thereof and it is to be understood that the invention is intended to be limited only as defined in the appended claims.

We claim:

1. A compound of the formula

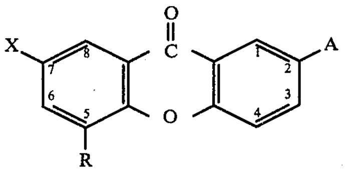

wherein A is —COOR', R' is selected from the group consisting of hydrogen, alkyl of 1 to 5 carbon atoms and cation of a non-toxic, pharmaceutically acceptable organic or inorganic base, R is selected from the group consisting of hydrogen, alkyl of 1 to 9 carbon atoms, alkoxy of 1 to 9 carbon atoms and alkoxy alkoxy of 2 to 9 carbon atoms and X is

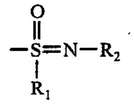

wherein $R_1$ is alkyl of 1 to 5 carbon atoms, $R_2$ is a carbamoyl.

2. A compound of claim 1 selected from the group consisting of 7-(N-carbamoyl-S-methylsulfonimidoyl)-xanthone-2-carboxylic acid and its alkyl esters of 1 to 5 alkyl carbon atoms and salts thereof with non-toxic, pharmaceutically acceptable bases.

3. A compound of claim 1 selected from the group consisting of 7-(N-carbamoyl-S-methylsulfonimidoyl)-5-(n-hexyl)-xanthone-2-carboxylic acid and its alkyl esters of 1 to 5 alkyl carbon atoms and salts thereof with non-toxic, pharmaceutically acceptable bases.

4. An anti-allergic composition comprising an effective amount of at least one compound of claim 1 and a pharmaceutical carrier.

5. A method of relieving allergic symptoms in warm-blooded animals comprising administering to warm-blooded animals and anti-allergically effective amount of at least one compound of claim 1.

6. The method of claim 5 wherein the active compound is selected from the group consisting of 7-(N-carbamoyl-S-methylsulfonimidoyl)-5-(n-hexyl)-xanthone-2-carboxylic acid and its alkyl esters of 1 to 5 alkyl carbon atoms and salts thereof with non-toxic, pharmaceutically acceptable bases.

* * * * *